United States Patent
Wolf et al.

(10) Patent No.: US 9,522,052 B2
(45) Date of Patent: Dec. 20, 2016

(54) DENTAL IMPLANT

(75) Inventors: Dietrich Wolf, Oberkochen (DE); Egbert Kremer, Hanau (DE)

(73) Assignee: FRIADENT GMBH, Mannheim (DE)

( * ) Notice: Subject to any disclaimer, the term of this patent is extended or adjusted under 35 U.S.C. 154(b) by 38 days.

(21) Appl. No.: 12/949,378

(22) Filed: Nov. 18, 2010

(65) Prior Publication Data

US 2011/0123949 A1    May 26, 2011

Related U.S. Application Data

(63) Continuation of application No. 11/884,037, filed as application No. PCT/EP2006/000907 on Feb. 2, 2006, now abandoned.

(30) Foreign Application Priority Data

Feb. 5, 2005 (DE) .................. 10 2005 005 402

(51) Int. Cl.
    *A61C 8/00*         (2006.01)

(52) U.S. Cl.
    CPC ............. *A61C 8/0066* (2013.01); *A61C 8/005* (2013.01); *A61C 8/0072* (2013.01); *A61C 8/0063* (2013.01); *A61C 8/0068* (2013.01); *A61C 8/0069* (2013.01); *A61C 8/0071* (2013.01)

(58) Field of Classification Search
    CPC ..... A61C 8/005; A61C 8/0063; A61C 8/0066; A61C 8/0068; A61C 8/0069; A61C 8/0071; A61C 8/0072; A61C 8/00
    USPC .................. 433/172, 174, 175, 176
    See application file for complete search history.

(56) References Cited

U.S. PATENT DOCUMENTS

| | | | | |
|---|---|---|---|---|
| 5,169,400 | A  * | 12/1992 | Muhling et al. ............... | 606/304 |
| 6,227,859 | B1 * | 5/2001 | Sutter .................... | A61C 8/005 |
| | | | | 433/173 |
| 2002/0177105 | A1* | 11/2002 | Engman ........................ | 433/173 |
| 2004/0033469 | A1* | 2/2004 | Blacklock ............ | A61C 8/0022 |
| | | | | 433/173 |

(Continued)

FOREIGN PATENT DOCUMENTS

| | | |
|---|---|---|
| JP | 11503655 | 3/1999 |
| JP | 2003518980 | 6/2003 |

(Continued)

*Primary Examiner* — Cris L Rodriguez
*Assistant Examiner* — Mirayda A Aponte
(74) *Attorney, Agent, or Firm* — Norris McLaughlin & Marcus, P.A.

(57) ABSTRACT

The invention relates to a dental implant comprising an implant body provided with a central receiving opening, a structural element provided with a journal engaging in the receiving opening, and a tension bolt which penetrates a borehole of the structural element and is screwed into an inner thread located in the receiving opening. First and second indexing elements are arranged in an apical region of the structural element, in order to pre-define the rotational position of the structural element in relation to the implant body. The at least one first indexing element is associated with the implant body or the structural element in a rotationally fixed manner, and at least two second indexing elements are associated with the structural element or the implant body in a rotationally fixed manner. The indexing elements extend especially at least partially into the region of the conical outer surface of the journal.

22 Claims, 9 Drawing Sheets

(56) References Cited

U.S. PATENT DOCUMENTS

2004/0101807 A1\* 5/2004 Porter .................. A61C 8/0001
433/173

FOREIGN PATENT DOCUMENTS

| JP | 2004283552 | 10/2004 |
|---|---|---|
| JP | 2004337536 | 12/2004 |
| WO | WO-2004/080328 | 9/2004 |

\* cited by examiner

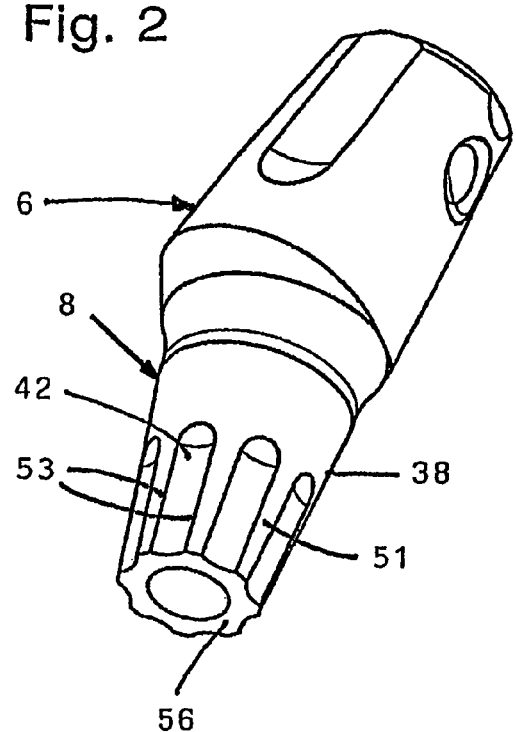
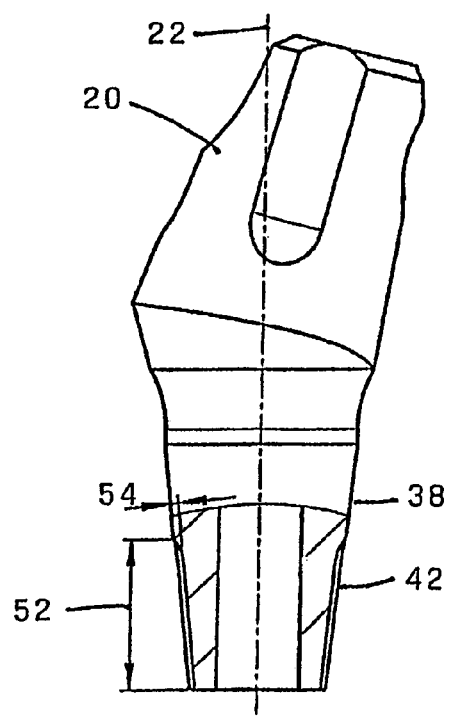

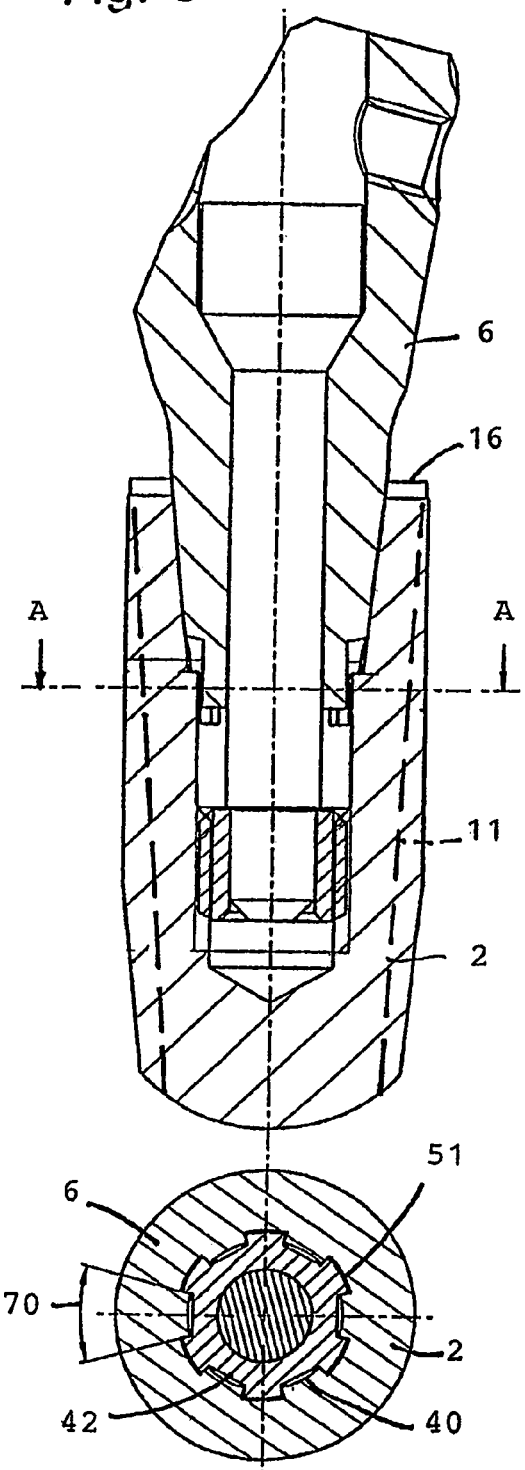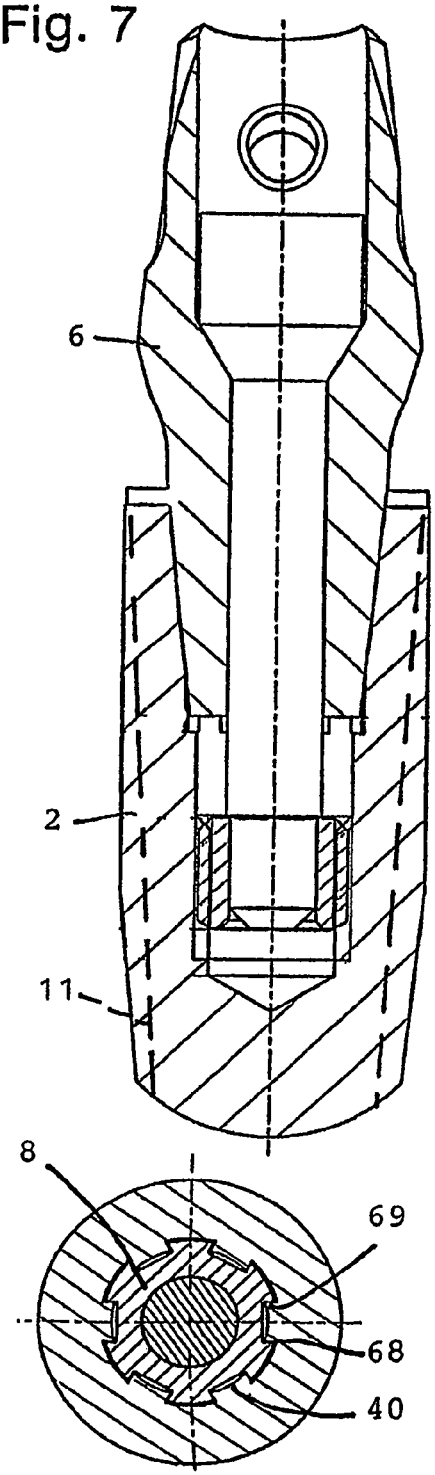
Fig. 6
Fig. 7
Fig. 8
Fig. 10

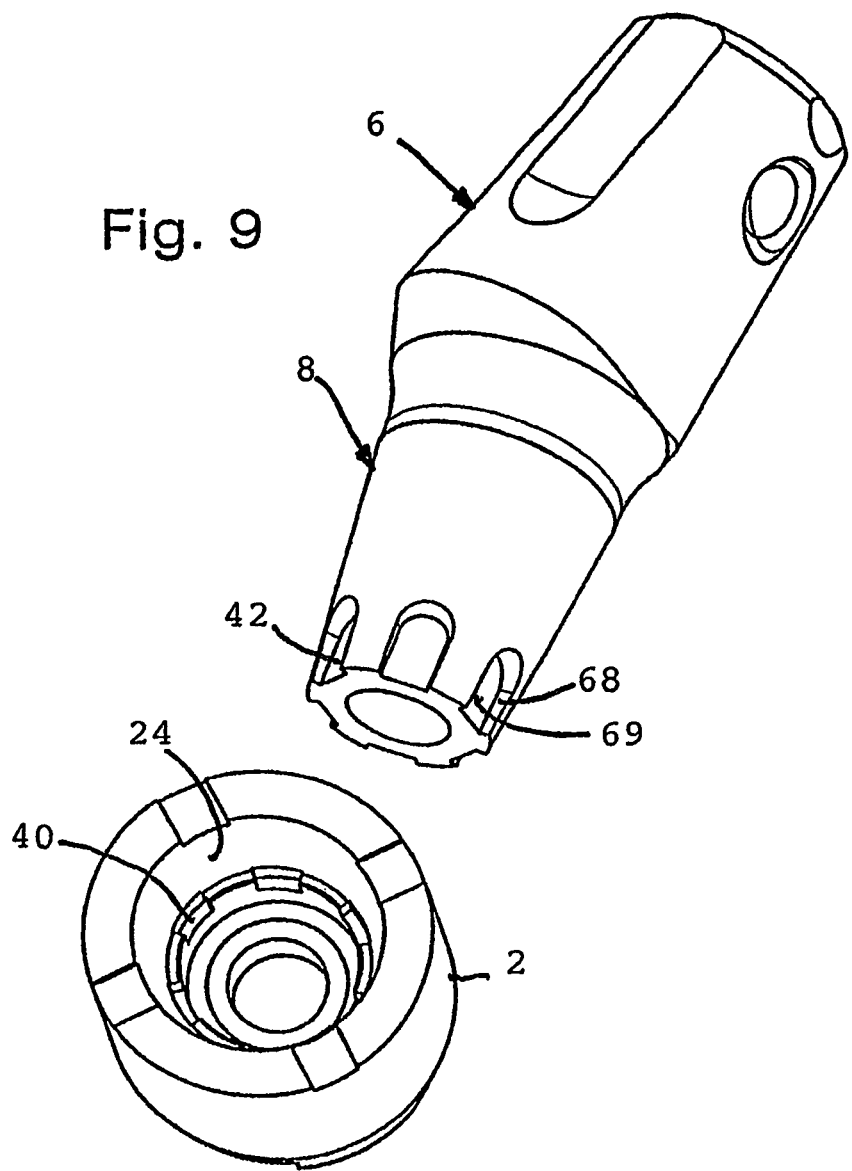

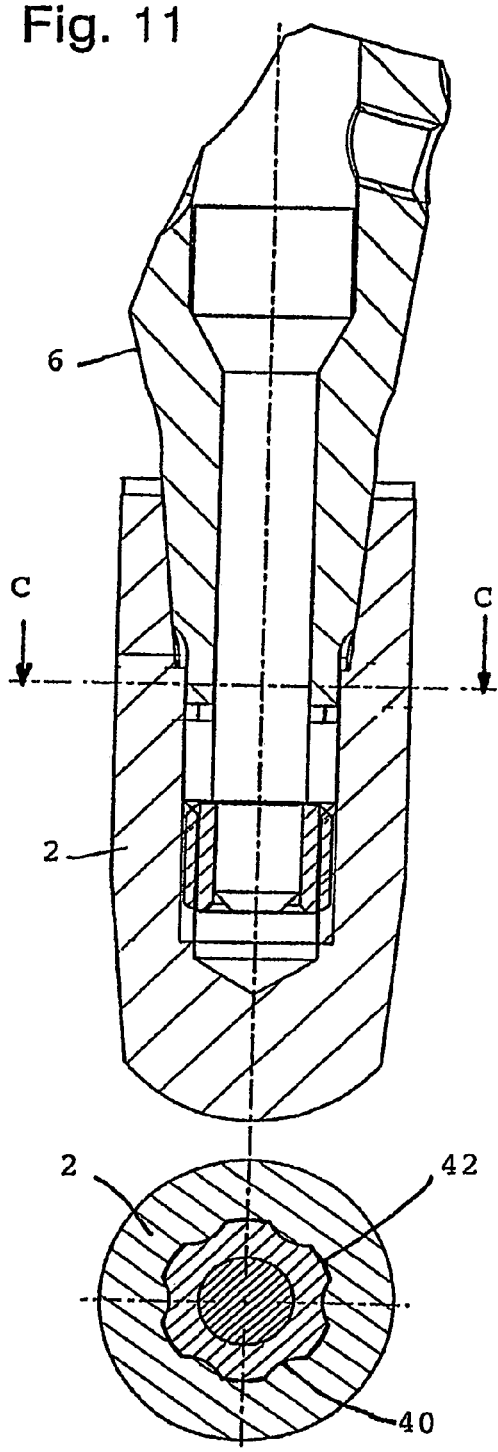
Fig. 11
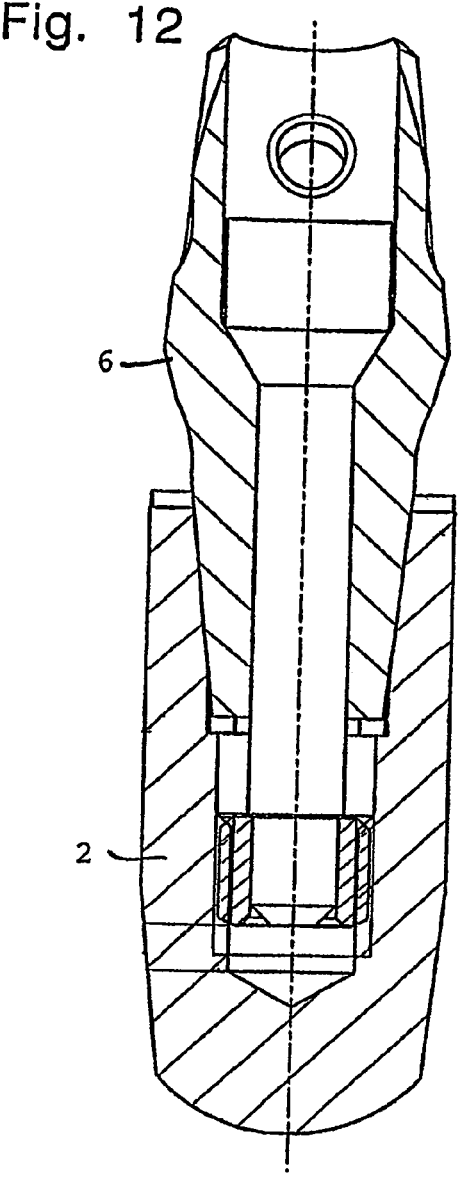
Fig. 12
Fig. 13

Fig. 15
Fig. 16
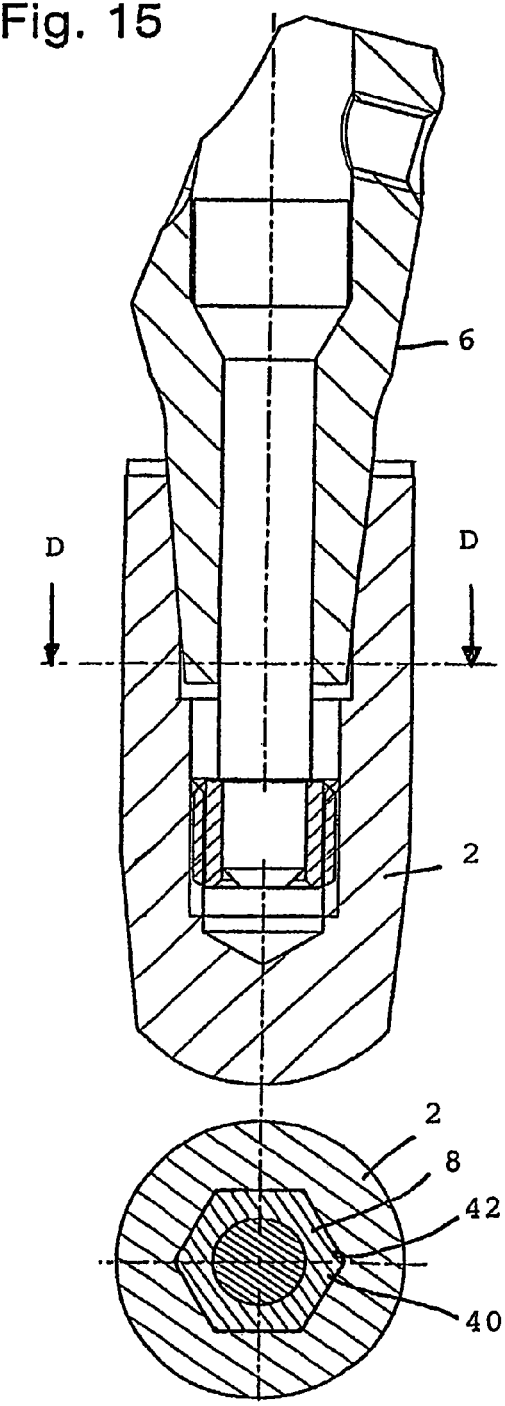
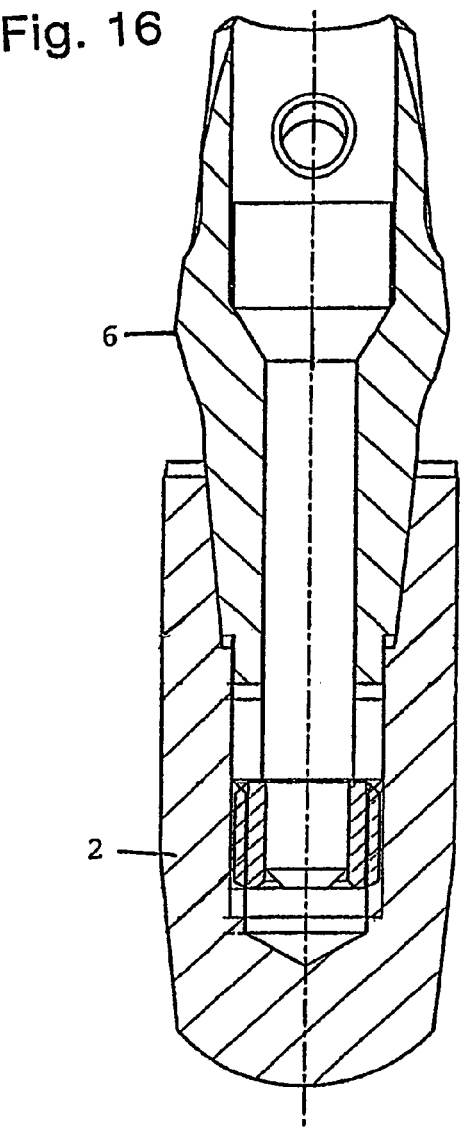
Fig. 17

DENTAL IMPLANT

BACKGROUND OF THE INVENTION

The invention relates to a dental implant.

Known from EP 0 707 835 B1 is such a dental implant that is embodied in two phases and has an implant body that can be anchored in the jawbone and a structural part that can be jointed thereto by means of a tension screw. The implant body contains a central receiving opening that has a conical inner surface opening to the coronal end and furthermore has in the inner end area an inner thread for anchoring the tension screw. The structural part contains a through-hole through which the tension screw passes, whereby in a head area of the structural part that faces the oral cavity the through-hole has an expansion for receiving a head of the aforesaid tension screw. The structural part furthermore contains a pin that engages at least partially in the receiving opening and that has a conical outer surface that matches the conical inner surface of the receiving opening. The aforesaid conical surfaces are advantageously embodied such that there is a self-locking cone connection between the implant body and the structural part joined by means of the tension screw. This positive-fit and form-fit conical connection ensures that the structural part is lastingly secure against rotation of the structural part with respect to the implant body, whereby functionally-secure tension is provided and/or ensured by means of the tension screw. Moreover, the gap-free and play-free conical connection reliably prevents bacteria and other pathogens from penetrating into the interior of the dental implant. For placing the implant body into an appropriately prepared opening or bore in the jawbone, the implant body contains in its coronal area or the coronal end surface placement elements for a placement tool, such as for instance occlusally opening slits for a screwdriver. In this two-phase dental implant, the structural part can be positioned steplessly with the implant body in terms of the longitudinal axis so that in particular special measures are necessary when impressions required for fashioning the superstructure and/or in the dental laboratory in order to maintain conformal alignment of the structural part relative to the implant body.

Furthermore, known from DE 94 17 182 U1 is an implant kit intended for tooth replacement, the implant body of which, when connected to the conical inner surface, has an indexing element embodied as a polygonal receiving element. Analogously, the structural part also contains, as an indexing element, a polygonal element in the axial direction adjacent to the conical outer surface. The conical inner surface is disposed inside a head part of the implant body, the aforesaid head part having an outer surface that expands conically toward the coronal end surface of the implant body. The indexing elements are disposed in an area in which the implant body does not have a thread on the outside. The implant body does not have an outer thread for anchoring in the jawbone until it is spaced axially from the indexing elements, and the outer thread extends from approximately the center of the longitudinal extension of the implant body to its apical end. Since the indexing elements are provided axially adjacent to the conical inner surface of the implant body, the conical inner surface of the implant body extends only across a small part of its entire length so that only a quite small and axially short connecting surface is available for the cone connection to the structural part.

Moreover, known from DE 299 20 283 U1 is an implant kit, the structural part of which, or where necessary a separate spacing element, can be fixed in the implant body in a rotationally stable manner via a cone connection and a central fixing screw or tension screw. The structural part is provided with a plurality of female molds in which a male mold of the implant body engages, in a rotationally stabilizing manner, as an indexing element in order to assure the structural position. The male mold pin is disposed in an axial area of the implant body in which the latter does not have a outer thread. In addition, the aforesaid area has only a short axial length in comparison to the entire length of the implant body, specifically largely in the quite short head area of the implant body. The aforesaid male mold pin is an additional component that projects radially from outside through the implant body into the area of the cone connection, whereby a not insignificant degree of complexity is required for precise arrangement and alignment.

Finally, known from DE 101 29 684 A1 is a structural part, called a tooth or jaw segment, on a base support or implant body. For joining the structural part to the implant body, an additional connecting element embodied as a double cone is provided that is inserted on the one hand into a conical recess of the structural part and on the other hand into a conical recess of the implant body. The double-cone connecting element has a positive-fit element corresponding to the implant body, whereby however the angle of rotation position of the structural part can be freely specified with regard to the double-cone connecting part. Conforming alignment of the structural part to the implant body is not possible.

The underlying object of the invention is therefore to further develop the dental implant of the aforesaid type having low structural complexity and/or structural volume such that in terms of the longitudinal axis a defined alignment, hereinafter referred to as indexing, of the structural part with respect to the implant body can be specified. The interactions and advantages for the aforesaid cone connection should also be retained. It should be possible to dimension and embody the dental implant according to the specific requirements in the different functional areas, such as in particular cone connection, indexing, thread connection. In addition, disadvantageous effects that various functional areas have on one another and in particular with respect to an outer thread should be avoided and the requirements in terms of loadability and/or service life should be lastingly satisfied to a large degree. Moreover, an uncomplicated implant system should be created that enables selectively on the one hand stepless adjustment of the rotation position or on the other hand a defined specification of the rotation position of the structural part with respect to the implant body.

SUMMARY OF THE INVENTION

The suggested dental implant is distinguished by a functionally appropriate design, whereby the rotation position of the structural part can be specified in a defined manner with respect to the implant body due, on the one hand, to the first and second indexing elements of the implant body, which correspond to one another and/or engage in one another, and due to the structural part, on the other hand. The indexing element or elements of the structural part are inventively arranged in its apical area, in particular the conical outer surface. Adjacent occlusally to the coronal end of the implant body is an annular zone that extends preferably largely to the coronal end surface and in which the conical outer surface of the structural part is positioned gap-free and play-free against the associated conical inner surface of the implant body. The aforesaid annular zone is preferably disposed at least in part in the area of the implant body in which the latter preferably has no outer thread. Alternatively, however, the implant body can also have no thread-free area in the coronal area, the outer thread advantageously having a shallower thread depth in the coronal area. In such embodiments, the aforesaid annular zone is thus disposed radially within the outer thread, in particular its thread area having a shallower thread depth. The indexing elements advantageously reach axially at least partially into the area of the conical surfaces of the pin and/or of the implant body, whereby conical surfaces are located in the circumferential direction between the indexing elements. The indexing elements are disposed axially largely in the area of the implant body in which the latter has an outer thread with a shallower depth than in the area of its apical end. Due to the inventively provided allocation of the indexing elements or parts thereof to the threaded area of the outer thread, in which the latter has a relatively shallow thread depth, the implant body has a wall thickness commensurate with the strength requirements, even when the outer diameter of the implant is small.

In a preferred manner, the inventive implant body has a thread-free area in the direction towards the coronal end adjacent to the outer thread and in particular its area having a shallower thread depth. After implantation of the implant body, this thread-free area and/or the coronal end of the implant body are disposed in a jawbone, at least approximately and/or largely in the area of the upper edge of the jawbone. In a preferred manner, an annular zone is disposed radially inward with respect to the aforesaid thread-free area, and in this annular zone the conical surface areas of the implant body and of the receiving part, which areas are embodied closed across the circumference, are positioned against one another under tension. In the alternative embodiment of the implant body without the thread-free area, the aforesaid annular zone also reaches at least approximately to the coronal end of the implant body. Moreover, the implant body is preferably embodied, at least in the coronal end area, with a largely cylindrical outer contour, whereby this area is embodied either thread-free or preferably with the outer thread having a shallower thread depth. The inventive implant body preferably does not have a head area expanded conically to the coronal end, which head area after implantation would be disposed inside and/or at least partially outside of the upper edge of the jawbone.

The placement and/or screw-in elements, preferably arranged in the coronal end area, in particular in the coronal end surface, of the implant body, are arranged spaced apart from the inventively provided indexing elements corresponding to the axial length of the aforesaid annular zone. It is of special significance that the placement elements on the one hand and the indexing elements on the other hand are embodied and arranged independent of one another and thus can be dimensioned corresponding to the requirements. Due to the inventive functional separation of the placement elements and the indexing elements, any changes in shape or damage to the placement elements during placement or screwing in of the implant body into the jawbone will not have any negative effects on the indexing or specification of the rotation position of the structural part with respect to the implant body.

The inventive dental implant advantageously has three functional areas that are independent of and/or separate from one another, specifically the placement elements on the coronal end area of the implant body, the annular zone having the conical surfaces of the structural part and of the implant body, which surfaces are located against one another closed tight and gap-free around the entire circumference, and the apical area with the indexing elements of the structural part and of the implant body, which indexing elements preferably engage one another in a positive fit.

In the framework of the invention, in one alternative embodiment, the placement and/or screw-in elements can be arranged within the implant body and/or within the central receiving opening. In this case, the placement and/or screw-in elements can be arranged interiorly at or near the coronal end just like in the interior of the receiving opening, like for instance between the indexing elements and the inner thread for the tension screw. In the framework of the invention, the placement and/or screw-in elements can also be combined with or embodied as the indexing elements of the implant body. Furthermore, in accordance with the invention the placement and/or screw-in elements can be integrated into the cone surface of the implant body and/or the latter can be used preferably in combination with an adapter. Such an adapter has an outer cone surface corresponding to the cone surface of the implant body and is joined in a suitable manner to the implant body for implantation thereof such that the forces or torques for placing and/or screwing in the implant body into the jawbone can be at least partially transmitted by means of the adapter via the aforesaid cone surfaces. Finally, in one special embodiment of the invention, the placement and/or screw-in elements can be embodied by combining the indexing element or elements of the implant body with its conical inner surface, in particular in combination with an adapter that has a corresponding conical outer surface and at least one corresponding indexing element. The aforesaid adapters are detachably joined to the implant body such that they can be removed from the implant body after the implantation.

In accordance with the invention, at least one first indexing element and furthermore at least two second indexing elements are present. Thus in one special embodiment the implant body has the at least one first indexing element that is embodied as a rib oriented radially inward towards the longitudinal axis, while the structural part has a specified number of the second indexing elements that are embodied as grooves in the apical area and/or in the conical outer surface of the structural part. Corresponding to the number of the second indexing elements of the structural part, the latter can assume a corresponding number of rotation positions or angle of rotation positions about the longitudinal axis with respect to the implant body. Preferably two first indexing elements are arranged diametrically.

In the framework of the invention, in one alternative embodiment the implant body can have a specified number of second indexing elements embodied as grooves, while the structural part has at least one first indexing element that is embodied as a rib that is oriented radially outward. It is obvious that for a number of the first indexing elements that is greater than 1 the angle distribution of the first indexing elements about the longitudinal axis and the angle distribution of the second indexing elements are matched to one another such that the structural part can be positioned in specified different angle of rotation positions with respect to the implant body.

In one special embodiment, the indexing element or elements are a component of an additional body, in particular a sleeve, that is fixed, rotation-fast, in particular in the apical area of the receiving opening, embodied as a blind borehole, of the implant body and is preferably pressed therein. Furthermore, in the framework of the invention a separately produced body can be joined rotation-fast at the apical end of the structural part and can have at least one indexing element that is preferably embodied as a rib and that projects into the area of the conical outer surface of the structural part. Such a body produced separately from the dental implant, whether separately from the implant body and/or the receiving part, ensures precise production and/or embodiment of the indexing elements. Alternatively, in the framework of the invention the indexing elements can be integral components of the implant body and/or of the structural part.

Moreover, the invention relates to an implant system having dental implants of the type indicated in the foregoing and in the following using the exemplary embodiments and furthermore more in the patent claims. The implant bodies have in particular different outer diameters and lengths for different indications. Moreover, the structural parts can above all have differently embodied head areas and/or the latter can be arranged at different angles to the longitudinal axis of the pin. The central receiving openings of the implant bodies on the one hand and the pins of the structural parts are embodied and/or matched to one another in the inventively suggested manner, however.

Suggested as a special embodiment of the invention is an implant system that includes structural parts, having the second indexing elements, which parts are embodied consistent for differently configured implant bodies. The implant system contains at least one implant body having the first indexing elements explained in the foregoing and furthermore at least one implant body without such indexing elements. These two types of implant bodies of the implant systems can, as is known, have different lengths and/or diameters, depending on the indication. In contrast, the structural parts that for their part can also be embodied differently, for instance with a head area coaxial with the pin or angled at different angles, are provided for both types of implant bodies. Thus it is possible to index the rotation position, or even to specify it in a stepless manner, depending on the medical indication, for the correctly embodied structural parts. In the inventive implant system, the same structural parts are used for the indexing and for the stepless adjustment of the rotation position, so that the complexity in terms of production, inventory, and supply is significantly reduced. If, moreover, separate bodies and/or the aforesaid sleeves are provided for the indexing elements, in particular in the implant body, the complexity of the implant body is significantly reduced, since apart from the separate body, the implant bodies are initially produced so that they are consistent and then depending on the purpose they are used for they are equipped with the separate body that has the indexing elements.

Moreover, suggested as an alternative special embodiment of the invention is an implant system that contains consistently embodied implant bodies for differently configured structural parts. This implant system thus contains at least one structural part having the first indexing elements explained in the aforesaid and at least one structural part without such indexing elements. Thus there are two types of structural elements present that in a known manner have different dimensions and designs depending on the indication, whereby the foregoing explanations regarding the implant having differently configured implant bodies apply analogously.

Further developments and special embodiments of the invention are provided in the subordinate claims and in the following description.

Special exemplary embodiments of the inventive dental implant are explained in greater detail using the drawings, without this resulting in limitations.

BRIEF DESCRIPTION OF THE DRAWINGS

FIGS. 2, 3 depict the structural part in perspective and in partial cut-away;

FIGS. 6-9 are sections and a perspective depiction of another exemplary embodiment of the dental implant having indexing elements embodied as toothed rings;

FIG. 10 is a section, similar to FIG. 8, but with modified tooth geometry;

FIGS. 11-14 are sections and a perspective depiction of another exemplary embodiment of the dental implant having indexing elements embodied as rounded teeth;

FIGS. 15-18 are sections and a perspective depiction of another exemplary embodiment of the dental implant having indexing elements embodied as hexagons.

DETAILED DESCRIPTION OF THE INVENTION

Figure 1:
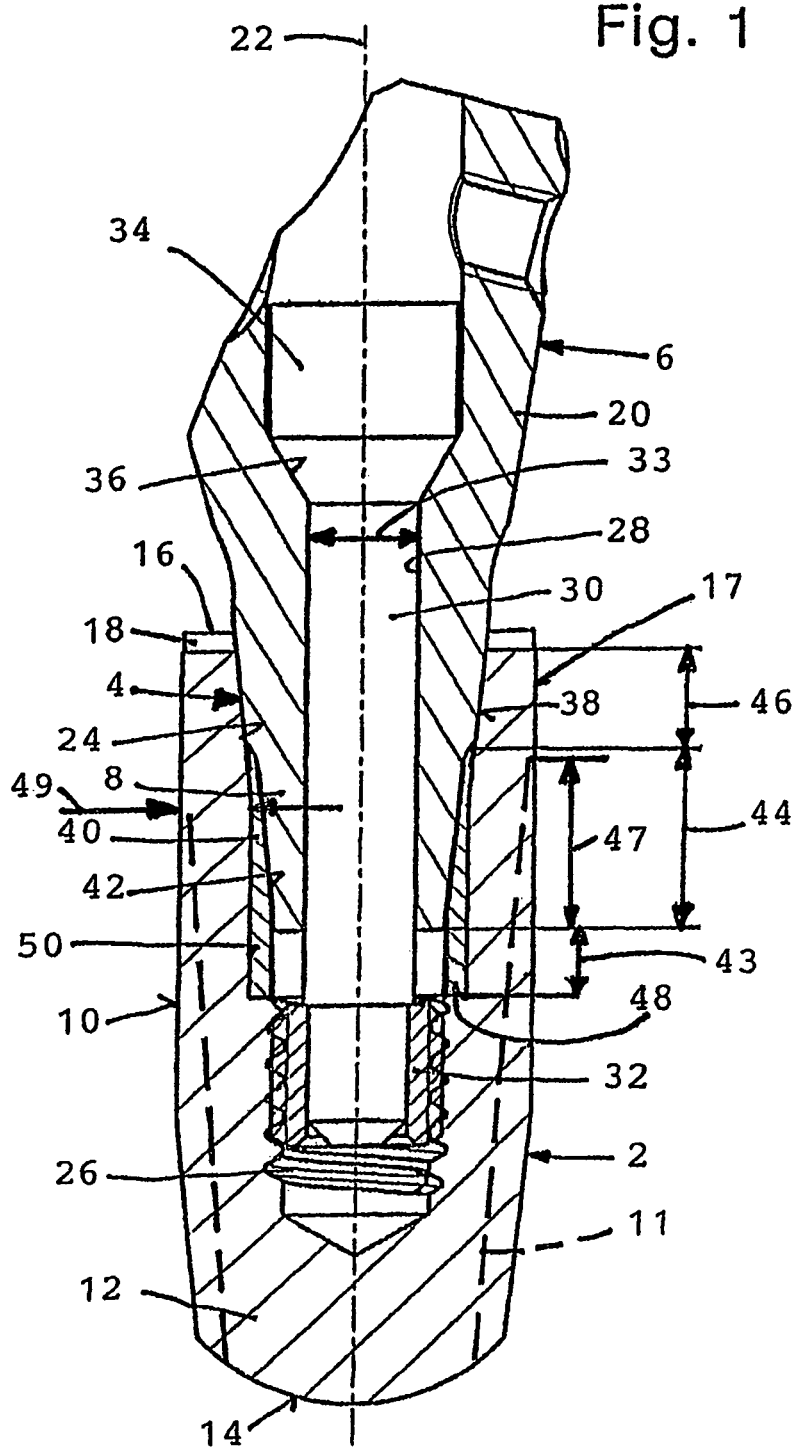
FIG. 1 depicts an axial longitudinal section of the dental implant.

In accordance with FIG. 1, the two-phase dental implant contains an implant body 2 having a central receiving opening 4 and a structural part 6, the pin 8 of which engages in the receiving opening 4. In its largely cylindrical outer surface 10 the implant body 2 is provided with an outer thread 11, indicated using the broken lines, and has at its apical end 12 a spherically rounded end surface 14. Proceeding from the apical end 12, which is to be inserted into the jawbone, the shape of the thread flank changes, preferably continuously, in the occlusal direction or toward the coronal end 16. In one special embodiment, the outer thread 11 has a thread core that tapers conically toward the apical end 12. Alternatively, the outer thread 11 and/or its core can be embodied in a stepped manner. Furthermore, the thread flank of the aforesaid thread oriented occlusally toward the coronal end 16 is advantageously embodied as a planar surface and the thread flank that changes shape and that is oriented apically is embodied in a curved, concave manner. Adjacent to the outer thread 11 in the direction of the coronal end 16, the implant body 2 advantageously has a thread-free area 17. At the coronal end 16 or in the coronal end surface present there the implant body 2 contains placement and/or screw-in elements 18 embodied as transverse grooves that make it possible to place and screw the implant body into the jawbone using an appropriate placement tool. It is expressly stated at this point that in the framework of the invention the outer geometry and/or the inner geometry of the implant body, whether its outer thread or the thread-free area or the placement and/or screw-in elements, can be embodied corresponding to the statements in the foregoing. The structural part 6 contains a head area 20 that projects out of the implant body 2 and that is angled at a specified angle to the longitudinal axis 22 and that serves to attach a superstructure or tooth replacement.

The central receiving opening 4, embodied as a blind hole, contains an inner surface 24 that proceeds largely from the coronal end 16 and that opens conically towards the latter and furthermore contains an inner thread 26 towards the apical end 12. A tension screw 30 passes through the structural part 6 that has a through-hole 28, which is coaxial with the longitudinal axis 22, and arranged at its inner end is a threaded sleeve 32, created for instance by laser welding. The threaded sleeve 32 has an outer diameter that is greater by a specified amount than the inner diameter 33 of the through-hole 28 and/or than the outer diameter of the part of the tension screw 30 that passes through the though-hole 28. The outer thread of the threaded sleeve 32 engages the aforesaid inner thread 26 of the implant body 2. As can be seen, the tooth tips of the threaded sleeve 32 are on a diameter that is significantly larger than the inner diameter 33 of the through-hole 28. In other words, the inner diameter 33 of the through-hole 28 can be embodied comparatively small so that a wall thickness for the pin 8 that is commensurate with the material and strength requirements is available for the indexing elements, which shall be explained in the following.

In the head area 20, the through-hole contains an expansion for receiving the screwhead 34, which is usefully positioned against a conically tapering support surface 36 such that when the tension screw 30 is tightened with a specifiable torque a defined tension of the structural part 6 is attained with respect to the implant body 2. For this, the conical outer surface 38 of the pin 8 engaging in the receiving opening 4 engages the conical inner surface 24 of the central receiving opening 4 with a specified tension. The takeout angles of the conical inner surface 24 and of the conical outer surface 38 are specified and/or embodied such that there is a self-locking cone connection. The cone connection is gap-free and play-free and assures lasting anti-rotation of the structural part 6 in the implant body 2.

Arranged in the central receiving opening 4 are first indexing elements 40 that are embodied as ribs oriented inward towards the longitudinal axis 22. The structural part 6 contains two indexing elements 42 embodied as grooves arranged in the conical outer surface 10. As can be seen, the first indexing elements 40 engage in the second indexing elements 42 in a positive fit . . . . The rotation position of the structural part 6 with respect to the implant body 2 is specified in a defined manner by means of the indexing elements 40, 42. Flat parts of the conical surfaces 24, 38 of the implant body 2 and of the pin 8 are positioned against one another, usefully under tension, in the circumferential direction between the indexing elements 40, 42. It is of special significance that the first and the second indexing elements 42 do not act against rotation but rather advantageously act exclusively to specify the rotation position and anti-rotation is assured by means of the aforesaid cone connection. The indexing elements 40, 42 are disposed in the interior of the central receiving opening 4 at a specified distance from the coronal end surface 16. It is of special significance that the indexing elements 40, 42 are arranged at a specified axial distance 43 from the inner thread 26 of the implant body and/or the outer thread of the tension screw that corresponds thereto and in particular its threaded sleeve 32. When joining the structural part 6 to the implant body 2 by means of the tension screw 30, this ensures that the apical end of the pin 8 reliably produces the required angle of rotation position of the structural part 6 with regard to the implant body 2 without limitation. It should furthermore be noted that the second indexing elements 42 are arranged in the apical area 44 of the structural part 6 and that between the apical area 44 and the coronal end 16 an annular zone 46 closed across the circumference is adjacent to the conical outer surface 38 play-free and gap-free at the conical inner surface 24 under tension. Also in the area of the placement elements 18, in which area the pin 18 enters the receiving opening 4, apart from the placement elements 18 embodied as radial grooves, the conical outer surface 38 or its surface parts are positioned against the conical inner surface 24 under tension. As can be seen, in the coronal end area and/or outside, in particular associated with the inner annular zone 46, the implant body 2 has a largely cylindrical outer contour, the thread-free area 17 preferably being there. However, in accordance with the above statements, the outer thread can alternatively also be provided with a preferably shallower thread depth, at least approximately to the coronal end 16. Preferably the inventive implant body 2 does not have a head area that expands conically towards the coronal end 16.

It is of special significance that the apical area 44 having the indexing elements 40, 42 is allocated at least partially and/or approximately to that part 47 of the outer thread 11 in which the latter has a shallower thread depth. In this axial area 47 of the outer thread, the implant body 2 possesses a wall thickness 49 that is adequate both in terms of strength requirements and stability requirements. This is of special significance particularly in implant bodies with comparatively small outer diameters. It should be noted that in the area 47 there is a significantly shallower thread depth compared to the thread depth in the apically adjacent area of the outer thread 11. Alternative to the depicted continuous transition due to the conical embodiment of the thread core of the outer thread 11, in the framework of the invention moreover a discontinuous and/or stepped transition from the area 47 to the apically adjacent further thread area of the outer thread 11 can be provided with a deeper thread depth.

The at least one first indexing element 40 is a component of a sleeve 48 that is fixed rotation-fast, and in particular non-detachably and/or by means of fixed joining, such as welding or adhesive, in a center area 50 of the receiving opening 4. The center area 50 is disposed axially between the conical inner surface 24 and the inner thread 26 of the receiving opening 4. The first indexing element or elements 40 project occlusally into the area of the conical inner surface 24.

FIGS. 2 and 3 depict the structural part 6, the pin 8 of which contains in the area of the conical outer surface 38 a number of the indexing elements 42 that are embodied as concave grooves and that are uniformly distributed across the circumference. In the circumferential direction between the indexing elements and/or grooves 42 the structural part 6 possesses conical surface parts 51 of the conical outer surface 38. The indexing elements 42 are inventively disposed radially inward and/or within the envelope curve, which is specified by the conical outer surface 38. In the area of the conical outer surface 38, the second indexing elements 42 or grooves have longitudinal edges 53 that are advantageously largely parallel. The indexing elements 42 extend in the axial direction at least partially into the conical outer surface 38 of the pin 8. On the other hand, the conical outer surface 38 with the conical surface parts 51 extends to the apical end 56 of the structural part. Due to the indexing elements 42 and the conical outer surface 38 at least partially engaging one another in the axial direction, an integration is created in a preferred manner in that across a substantial total axial length of the pin 8 there is overlap of the conical outer surface 38 and/or its surface parts 51 with the correspondingly embodied conical inner surface of the implant body 2 without the pin 8 being required to have a significantly enlarged total length, which would have been necessary in the case of an addition to the axial cone length and the axial length of the indexing elements arranged thereafter. Due to the inventive at least partially axial and/or radial integration of the indexing elements 42 into the conical outer surface 38, a functionally reliable conical coupling is assured in a preferred manner while retaining and/or attaining a relatively short total length of the pin 8.

The grooves 42 are arranged at a specified angle to the longitudinal axis 22, this angle largely corresponding to half the takeout angle of the conical outer surface 38. As can be seen, the second indexing elements or grooves 42 extend only over a part of the total length of the conical outer surface 38, the axial extension 52 being for instance on the order of magnitude of 2 mm. The grooves 42 have depth 54, preferably on the order of magnitude and/or ranging from 0.1 to 0.6 mm, in particular on the order of magnitude of and/or ranging from 0.2 to 0.4 mm. The grooves 42 are embodied open at the apical end 56 of the structural part 6 so that when the structural part 6 is being placed the allocated indexing element or elements of the implant body 2 can be introduced therein into the grooves 42 with no problem.

Figure 4:
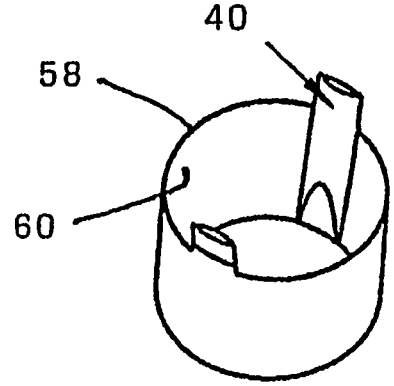
FIGS. 4, 5 depict the body having two indexing elements and produced separately embodied as a sleeve.
Figure 5:
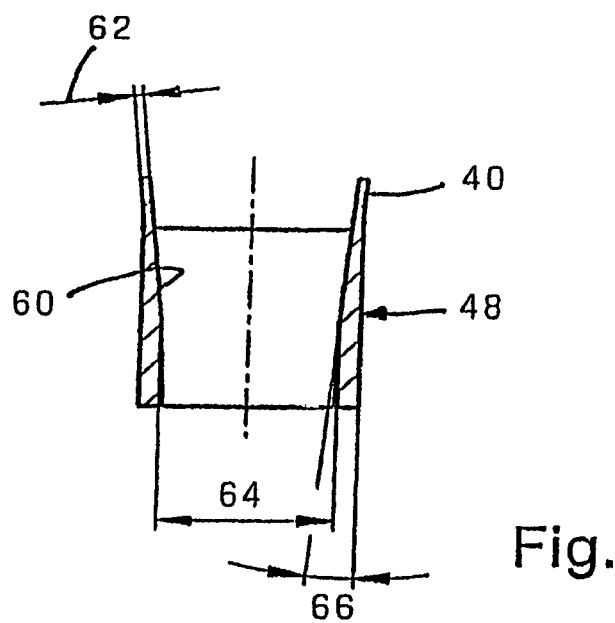
Figure 14:
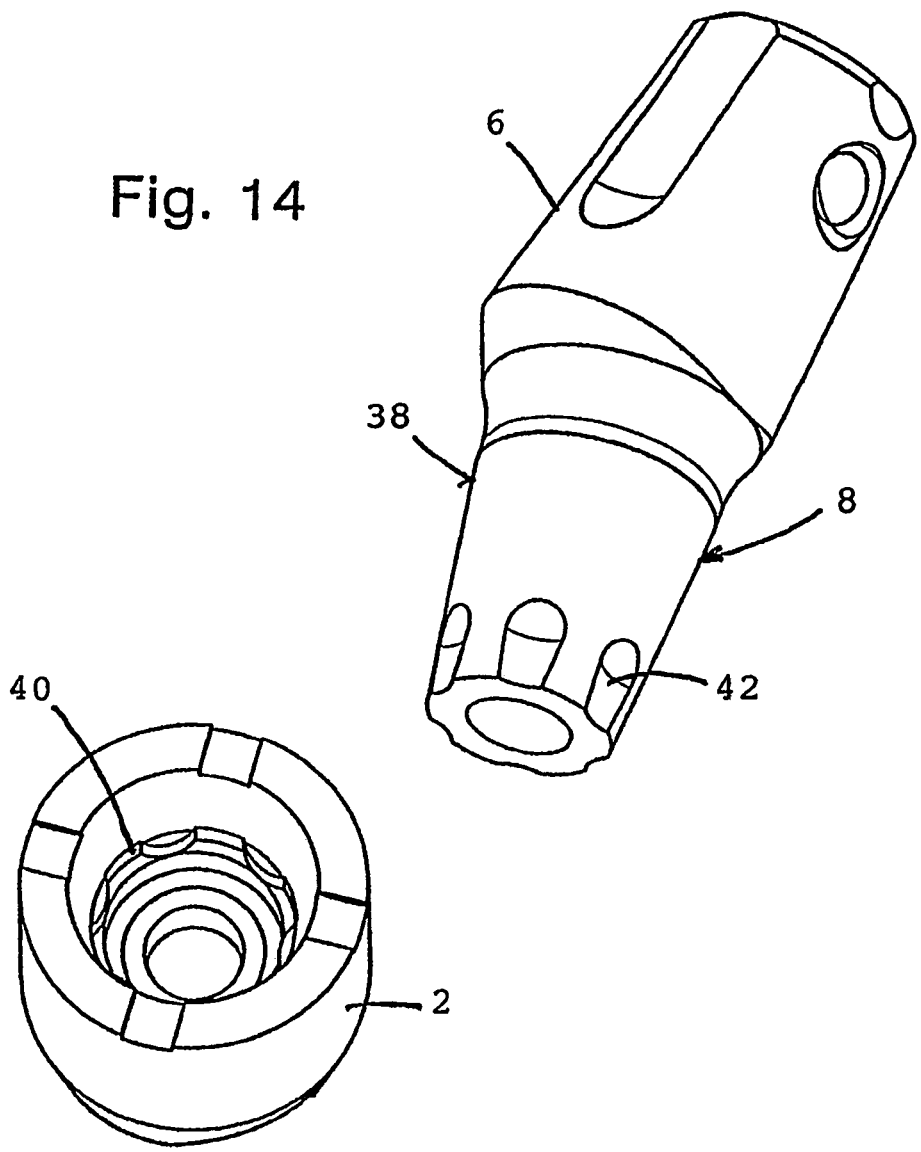
Figure 18:
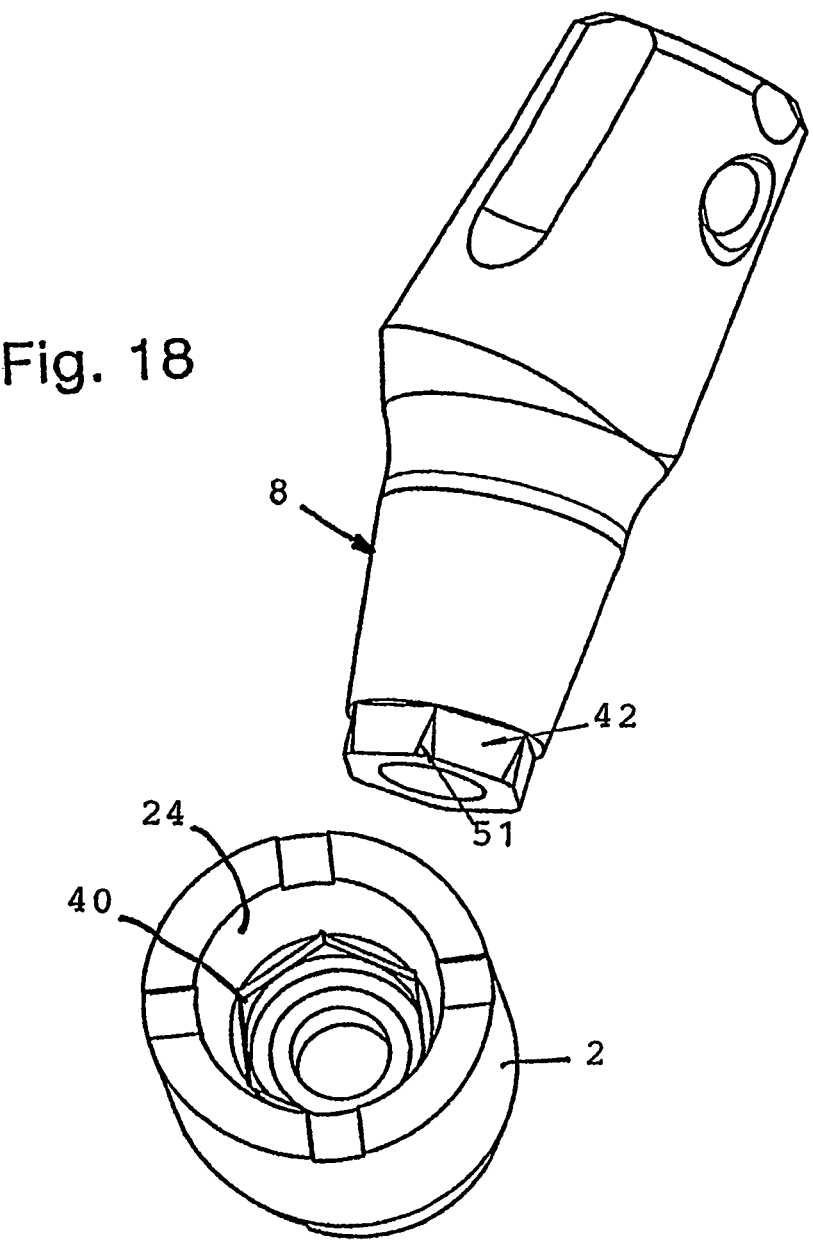

FIGS. 4 and 5 depict the body, embodied as a separate sleeve 48, of the implant body. The sleeve 48 contains two diametrically arranged indexing elements 40 that are embodied as ribs. The ribs 40, oriented radially inward, have a convex surface corresponding to the grooves, explained in the foregoing, of the structural part. As can be seen, the ribs 40 project in a specified length beyond the occlusally oriented upper edge 58 of the sleeve 48. At least a portion of the part of the inner surface 60 of the implant or of the conical outer surface of the structural part that is oriented apically from the edge 58 is also embodied conical. At their free ends the ribs 42 have a thickness 62 that is preferably on the order of magnitude of and/or ranges from 0.1 to 0.6 mm, in particular on the order of magnitude of and/or ranges from 0.2 to 0.4 mm. In this special embodiment, the inner diameter 64 of the sleeve 48 preferably ranges from and/or is on the order of magnitude of 1.5 to 2.3 mm, preferably 1.6 to 1.9 mm, in particular approximately 1.75 mm, while the angle of inclination 66 of the inner surface 60 is at least approximately 5.7°.

The exemplary embodiment of the dental implant in accordance with FIGS. 6 through 9 is fundamentally the same as the dental implant explained in the foregoing having the implant body 2 and the structural part 6 with the pin 8, whereby FIG. 8 depicts a section transverse to the longitudinal axis in accordance with sectional line A in FIG. 6. The indexing elements 40, 42 are embodied as mutually engaging toothed rings of the implant body and pin 8. As can be seen, the indexing element 40 of the implant body 2 contains teeth 40 as ribs and oriented radially inward and corresponding herewith the pin 8 contains the indexing elements 42 embodied as grooves. The grooves 42 each contain opposing lateral walls 68, 69 that are arranged at a specified angle 70 that opens outward radially. The angle 70 is advantageously specified at least approximately at about 30°. As teeth, the first indexing elements 40 are integral components of the implant body 2. The implant body 2 has the outer thread 11, which in this embodiment reaches at least approximately to the coronal end 16, there not being a thread-free area. However, alternatively, as explained using FIG. 1, the outer thread can terminate prior to the coronal end and the implant body 2 can have the aforesaid thread-free area. This also holds true for the other exemplary embodiments. Moreover, the different embodiments of the inventive dental implant can be embodied with another outer geometry, in particular with respect to the outer thread, whereby instead of the depicted, largely conical thread core, the thread and/or the thread core can be embodied non-continuous and/or with at least one step.

FIG. 10 depicts another embodiment of the toothed rings or indexing elements 40, 42. In this case, the lateral walls 68, 69 are arranged largely parallel to one another. It should be noted that in the framework of the invention further indexing elements or toothed rings are disposed with a different distribution and number of teeth and/or grooves and ribs.

In the embodiment of the dental implant in accordance with FIGS. 11 through 14, FIG. 13 depicting a section along section line C in accordance with FIG. 11, the indexing elements 40, 42 are again embodied as teeth that engage in one another. The teeth or ribs and grooves in this case are arched or rounded with specified radii. As can be seen from FIG. 14, in this embodiment, as well, the grooves 42 of the pin 8 are arranged radially within the envelope curve specified by the conical outer surface 38.

Finally, the exemplary embodiment in FIGS. 15 through 18 contains hexagonal indexing elements 40, 42, as can be seen in particular from FIG. 17, which depicts a section along section line D in accordance with FIG. 15. In accordance with FIG. 18, the indexing elements 42 of the pin 8 are disposed inside of the envelope curve of the pin 8 that is specified by the conical outer surface 38. In accordance with FIG. 18, the conical surface parts 51 are present between the hexagonal surfaces of the indexing elements 42.

The invention claimed is:

1. A dental implant comprising an implant body, a structural part, and a tension screw;
   wherein the implant body comprises an apical end and a coronal end; an apical area, and, proximal to a coronal end of the apical area, a thread free annular zone; and a central receiving opening extending along a longitudinal axis of the dental implant;
   wherein the structural part comprises a pin and a head area, the pin extending into the central receiving opening of the implant body, an entirety of the head area being external to the coronal end of the implant, body;
   wherein an entire length of the pin that is within the central receiving opening has a constant longitudinal slope along said entire length so as to have a conical shape from one end toward the head area to a longitudinally opposite end away from the head area of the structural part;
   wherein the pin comprises an annular portion nearest to the head area and an indexing portion adjacent to the annular portion, the indexing portion comprising in a circumferential direction recessed portions alternating with non-recessed portions, each one of the recessed portions being a longitudinally extending groove defining a second indexing element, each one non-recessed portion of the non-recessed portions extending from the annular portion so that said pin has said constant longitudinal slope from said one end of the pin to said longitudinal y opposite end of the pin along a length encompassing said one non-recessed portion;
   wherein the head area of the structural part has an external surface that is angled relative to the longitudinal axis and being configured to receive a structure of a tooth replacement;
   wherein the tension screw passes through a through-hole of said structural part and is screwed into an inner thread present in said receiving opening;
   wherein said implant body further comprises first indexing elements each one first indexing element configured to mate with a corresponding one of said second indexing elements to provide a circumferential indexing of the structural part relative to the implant body;
   wherein an entire length of said annular portion of said pin is situated within said central receiving opening;
   wherein said annular portion and each one non-recessed portion of the non-recessed portions extending from the annular portion which together have said constant longitudinal slope from said one end of the pin to said longitudinally opposite end of the pin together form a tapered cone, which tapered cone has a tight fit with a conical inner surface of said implant body along an entire circumference and length of the annular portion and along an entire length of each one non-recessed portion, so as to provide rotational locking of the structural part relative to the implant body, which tight fit is configured to prevent rotation of the structural part relative to the implant body, said tight fit comprising an external diameter of the pin being greater than an internal diameter of said central receiving opening of said implant body along said entire length of contact between said annular portion and said central receiving opening and between said entire length of contact between said each one non-recessed portion and said central receiving opening;

wherein said mating of said first indexing element and second indexing element is less than a tight fit so as to provide for a rotational position without providing rotational locking of the structural part relative to the implant body at a contact area between the first indexing element and second indexing element; and wherein for anchoring in the jawbone, said implant body has an outer thread having an area having a shallower thread depth compared to the thread depth of the outer thread in the apical area that is adjacent and/or allocated to said apical end of said implant body and wherein said first indexing elements are allocated to said area of the outer thread having shallower thread depth.

2. A dental implant comprising:

an implant body having a coronal end surface at a coronal end, an apical end, a central receiving opening extending along a longitudinal axis of the dental implant, an apical area, and an outer thread extending from the apical end and terminating in the apical area, whereby, proximal to a coronal end of the apical area, an annular zone, free of outer thread, remains;

a structural part having a center through-hole through the entire length of the structural part, and comprising a pin portion that is received in engages in said central receiving opening of said implant body, and a head area external to the coronal end of the implant body, the pin portion comprising a conical portion tapering to an apical area, an entire length portion of the pin that is within the central receiving opening having a constant longitudinal slope along said entire length so as to have a conical shape from one end toward the head area to a longitudinally opposite end away from the head area of the structural part;

the head area having an external surface that is angled relative to the longitudinal axis and being configured to receive a structure of a tooth replacement; and a tension screw fitted with a threaded sleeve at an apical end thereof and that passes through the entire length of the through-hole of said structural part and is screwed into an inner thread present proximal an apical end of said receiving opening;

said implant body having first indexing elements, and having transverse groove placement elements in the coronal end thereof for placing said implant body in a jawbone, and wherein a conical inner surface of said implant body is in contact with a conical outer surface of said pin adjacent thereto under tension to form a cone connection that provides for anti-rotation of said structural part with respect to said implant body, wherein, in the apical area of said structural part, an indexing portion comprising a plurality of second indexing elements are arranged at the conical portion of the pin portion for specifying the rotation position of said structural part with respect to said implant body, each one first indexing element configured to mate with a corresponding one of said second indexing elements to provide a circumferential indexing of the structural part relative to the implant body;

wherein the pin comprises an annular portion nearest to the head area and an indexing portion longitudinally adjacent to the annular portion, the indexing portion comprising in a circumferential direction recessed portions alternating with non-recessed portions, each one of the recessed portions being a longitudinally extending groove defining a respective one of the second indexing elements, each one non-recessed portion of the non-recessed portions extending from the annular portion so that said pin has said constant longitudinal slope from said one end the pin to said longitudinally opposite end of the pin along a length encompassing said one non-recessed portion;

wherein the first indexing elements are affixed to said implant body;

wherein the second indexing elements are located on the structural part and disposed radially inward at an angle coincident with the cone angle of the conical outer surface of the pin portion of said structural part;

wherein said first indexing elements extend into the area of said conical outer surface of said pin portion, but do not extend into the annular zone, the annular zone being an inner threadless annulus, free of said first and second indexing elements, and extending longitudinally along the central receiving opening at the coronal end of the implant body proximal to said coronal end of the apical area; and wherein an entire length of said annular portion of said pin is situated within said central receiving opening;

wherein said annular portion and each one non-recessed portion of the non-recessed portions extending from the annular portion which together have said constant longitudinal slope from said one end of the pin to said longitudinally opposite end of the pin together form a tapered cone, which tapered cone has a tight fit with a conical inner surface of said implant body along an entire circumference and length of the annular portion and along an entire length of each one non-recessed portion, so as to provide rotational locking of the structural part relative to the implant body, and which tight fit is configured to prevent rotation of the structural part relative to the implant body, said tight fit comprising an external diameter of the pin being greater than an internal diameter of said central receiving opening of said implant body along said entire length of contact between said annular portion and said central receiving opening and between said entire length of contact between said each one non-recessed portion and said central receiving opening;

wherein for each one of said second indexing elements, surface area of the conical portion between said each one of said second indexing elements and an adjacent one of said second indexing elements is oriented to define said conical portion tapering and is a continuous surface defining a conical shape of the conical portion;

wherein the annular zone is an inner threadless annulus, free of said first and second indexing elements, extending longitudinally along the central receiving opening at the coronal end of the implant body proximal to said coronal end of the apical area, and located longitudinally between the coronal end of the implant body to one longitudinal end of the annular zone and the apical area and a portion including the first indexing elements and second indexing elements beyond a second longitudinal end of the annular zone;

wherein all of the first indexing elements and second indexing elements are located closer to the apical end of the implant body than the annular zone; and wherein for anchoring in the jawbone, said implant body has an outer thread having an area having a shallower thread depth compared to the thread depth of the outer thread in the apical area that is adjacent and/or allocated to said apical end of said implant body and wherein said first indexing elements are allocated to said area of the outer thread having shallower thread depth.

3. The dental implant of claim 1, wherein said conical outer surface of said pin of said structural part is positioned across its entire circumference against said conical inner surface of said implant body, and/or in said apical area in a circumferential direction between said second indexing elements said conical outer surface is positioned against said conical inner surface.

4. Dental implant in accordance with claim 3, wherein provided in the direction toward the corona end of said implant body adjacent to said outer thread is a thread-free area and said annular zone is situated at least partially radially inward to said thread-free area and within the annular zone said conical inner surface is closed across the circumference and is positioned against said conical outer surface of said pin and/or said annular zone is arranged at least partially radially inside of the area in which said outer thread of said implant body has a shallower thread depth radially outward.

5. Dental implant in accordance with claim 4, wherein a thread sleeve is arranged on the apical end of said tension screw and engages in said inner thread of said receiving opening of said implant body, and an outer diameter of said thread sleeve is larger than an outer diameter of said tension screw.

6. Dental implant in accordance with claim 1 or 2, wherein said apical area is provided at a specified distance spaced apart from said coronal end of said implant body and/or said placement elements arranged there.

7. The dental implant of claim 6, wherein said specified distance corresponds to said length of said annular zone.

8. The dental implant according to either of claim 1 or 2, wherein said first and second indexing elements are arranged at a specified axial distance from said inner thread of said implant body and/or said outer thread of said tension screw.

9. The dental implant according to claim 8, wherein said specified axial distance is from said outer thread of said tension screw.

10. The dental implant in accordance with claim 1, wherein at least two of said first indexing elements are ribs, each of said ribs projecting beyond one of said conical surfaces, at least two of said second indexing elements are grooves in the other of said conical surfaces, and said ribs and grooves are arranged at an angle to a longitudinal axis of said dental implant that is substantially the same as said conical inner surface and/or said conical outer surface.

11. The dental implant of claim 1, wherein said first indexing elements are integral components of said implant body and said second indexing elements are integral components of said structural part.

12. The dental implant of claim 1, wherein said second indexing elements are in the form of grooves in said pin and are arranged radially inside an envelope curve that is specified by the conical outer surface of said pin.

13. Implant system comprising two or more dental implants in accordance with claim 1, wherein an outer geometry for each implant body among said two or more dental implants is mutually different and wherein for each implant body among said two or more dental implants and for each structural part among said two or more dental implants, the pin of said each structural part is matched to the central receiving opening of said each implant body.

14. The implant system of claim 13, wherein a first one of the two or more dental implants differs in length and/or diameter from at least another one of the two or more dental implants.

15. Implant system comprising the dental implant according to claim 1, wherein said structural part is a first structural part, and further comprising at least one additional structural part that does not have any of said second indexing elements, and wherein said implant body is selectively joined to said first structural part or to said at least one additional structural part.

16. The implant system of claim 15, wherein the first structural part differs in length and/or angling of head areas thereof with respect to a longitudinal axis thereof from at least one of said at least one additional structural part, and wherein said at least one additional structural part comprises a plurality of second structural parts that do not have any indexing elements and that differ in length and/or angling of head areas thereof with respect to the longitudinal axis thereof.

17. The dental implant of claim 1, wherein the placement elements are situated in an area of said corona end of said implant body.

18. The dental implant according to claim 1, said first indexing elements are components of a separate body that is joined to said implant body, wherein said separate body is a sleeve arranged in a center area of said implant body and said inner thread of said receiving opening is apically adjacent to said center area.

19. The dental implant of claim 1, wherein the first indexing elements are affixed to said implant body, and the second indexing elements are affixed to said structural part.

20. The dental implant of claim 1, wherein the first indexing elements do not extend completely to the coronal end of the implant body.

21. The dental implant of claim 2, wherein the first indexing elements are ribs fixedly attached to the implant body and the second indexing elements are grooves located on the structural part and disposed radially inward at an angle coincident with the cone angle of the conical outer surface of the pin portion of the structural part.

22. The dental implant of claim 2, wherein the first indexing elements do not extend completely to the coronal end of the implant body.

* * * * *